Figure 1:
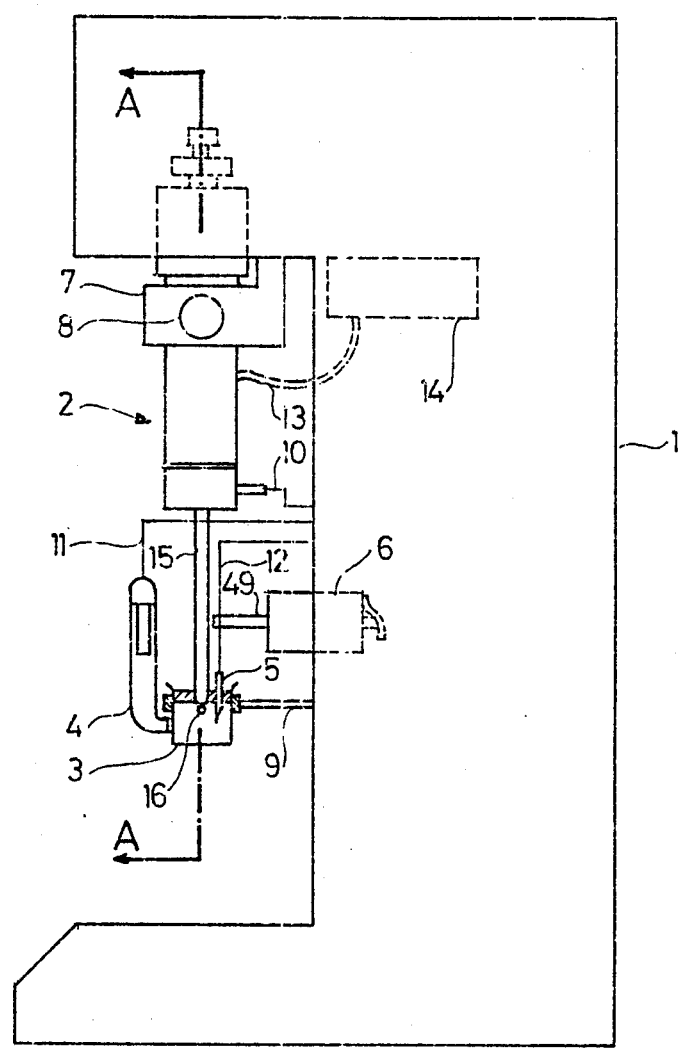

United States Patent [19]

Nagy et al.

[11] Patent Number: 4,939,410
[45] Date of Patent: Jul. 3, 1990

[54] ELECTRODE ARRANGEMENT WITH LIQUID-METAL ELECTRODE OF CONTROLLABLE SURFACE

[75] Inventors: Géza Nagy; József Tarcali; Erno Pungor; Klára Toth; Veronika, nee Mohacsi Karpati; Zsófia Fehér; Gyorgy Horvai; Peter Sarkany; István Bokor, all of Budapest, Hungary

[73] Assignee: Magyar Tudományos Akadémia Kutatás- és Szervezetelemzo Intézete, Budapest, Hungary

[21] Appl. No.: 249,742

[22] Filed: Sep. 27, 1988

[30] Foreign Application Priority Data

Oct. 5, 1987 [HU] Hungary .............. 4464/87

[51] Int. Cl.$^5$ .................. H01J 13/10; H01J 13/14; G01N 27/34
[52] U.S. Cl. .................. 313/231.01; 313/163; 313/172; 313/29; 204/413
[58] Field of Search .......... 313/231.01, 163, 172, 313/29; 204/413; 313/29

[56] References Cited

U.S. PATENT DOCUMENTS 3,579,011 5/1971 Hyman, Jr. .................. 313/29
4,260,467 4/1981 Smith et al. .................. 204/413

FOREIGN PATENT DOCUMENTS 220439 9/1982 Czechoslovakia .

OTHER PUBLICATIONS

American Laboratory, "Static Mercury Drop Electrode", Peterson, Dec. 79, pp. 69–78.
Dissertation of Mr. L. Novotny, Prague 12/1981, pp. 155 and 157.
Statische Tropfenelektrode SMDE, prospectus of the firm Laboratorni Pristroje, Prague, 12/1981.
Universal Mercury Mini-and Microelectrode UM-ME-1 prospectus of the firm Labora, Prague, 12/1987.

*Primary Examiner*—Kenneth Wieder
*Attorney, Agent, or Firm*—Jordan and Hamburg

[57] ABSTRACT

Electrode arrangement with liquid-metal electrode of controllable surface, comprising a liquid-metal reservoir, a capillary connected thereto through a controllable valve and contact means being in electric contact with the liquid-metal in the capillary. According to the invention at least one section of the capillary is formed within a metal body not reacting chemically with the liquid-metal, said metal body constituting the contact means. Preferably, the metal body is formed so that an elastic closing element of the valve fits to a surface of the metal body surrounding an opening of the capillary section formed therein.

9 Claims, 3 Drawing Sheets

ELECTRODE ARRANGEMENT WITH LIQUID-METAL ELECTRODE OF CONTROLLABLE SURFACE

The invention relates to an electrode arrangement with liquid-metal electrode of controllable surface which is suitable for determining the concentration of ions and molecules.

For classical polarographic measurements mercury electrodes continuously dropping upon hydrostatic pressure were used. In addition to the advantageous characteristics of the dropping mercury electrode several unfavorable features can be observed. As a consequence of the continuously changing drop surface a condenser-current is flowing through the electrode as a disturbing signal, furtheron, resulting from dropping a so-called capillary-effect occurs. Said phenomena gain considerable importance mainly with analytic measurements performed in the range of lower concentrations, thus reducing sensitivity and reproducibility of determinations.

To eliminate the above mentioned disturbing phenomena a repeatedly renewable mercury electrode was developed which had a constant surface area during measurement. By this solution the efficiency of polarographic methods could be considerably increased. In consequence of the constant size of the mercury drop in the course of measuring disturbing condenser-current resulting from changes in surface area does not occur. It can be prevented that the size of the drop is influenced by the electrode potential through influencing the surface tension. The size of the drop and the useful life thereof can be varied in an utmost wide range. Such electrode arrangements may be realized by a needle valve or a plate valve.

In a known electrode arrangement having a needle valve there are a mercury reservoir and a glass capillary forming the mercury drop. The end of the capillary facing the mercury reservoir is cone-shaped with a valve needle therein, which is arranged so that in closed position the valve needle closes the path of the mercury to the capillary. The valve needle is actuated by means of a spring and an electromagnet. It is also the task of the valve needle to establish—as electric contact means—the electric connectin between the mercury and a line connected to the input of a measuring unit.

In a known electrode arrangement having a plate valve the layout is similar to that of the arrangement with needle valve. In this case too the glass capillary is built together with the mercury reservoir, however, the end of the capillary facing the reservoir is closed with a plate valve comprising a closing element made of rubber. The plate valve is also actuated by a spring and an electromagnet. An annular electrically conductive tin dioxide film formed on the surface of the endplate of the glass capillary facing the mercury reservoir establishes the contact between the input line of the measuring unit and the mercury drop.

With the known mercury electrode arrangements having constant drop surface it is considered as disadvantageous that mercury electrodes get damaged within a relatively short time in spite of careful manipulation and the application of expensive mercury of high purity is imperative.

In the arrangement with the needle valve the metal needle contacts the cone-shaped part of the glass capillary on a relatively small surface, therefore the pressure exerted by the closing spring is high. However, if a lower pressure is chosen, safe closure could not be achieved, a flow might occur after closure. Additionally, the high spring pressure is built-up very quickly as by ceasing the effect of the electromagnet opening the valve the spring closes with a momentary action. Due to the sudden force either the glass capillary or the valve needle frequently breaks. Even if failure can be avoided, after a relatively short duration of operation the shape of the valve needle will change due to wear, accordingly closing of the path of mercury becomes uncertain and the environment of the valve will be contaminated with metal powder. At the same time the metal powder causes leakage, the path of mercury cannot be closed with the required certainty. Upon the effect of impacts the glass capillary is crumbling to dust, too, as a consequence insulating powder thereof causes uncertainity in respect of electric contact.

Primary cause of deficiency of the known arrangement having a plate valve lies in the tin dioxide film used as electric conductor. Tin dioxide is chemically instable, in the course of use it becomes inhomogeneous due to decomposition, its resistance increases, and accordingly, as an electric conductor it will be unreliable. A further disadvantage is that due to the motion of the closing element the thin film is wearing away within a relatively short time, as a consequence the electric conductivity ceases. A further unfavorable feature of the known solution lies in that sulphur component of the rubber closing element of the plate valve reacts with the mercury resulting in its contamination.

A further drawback of both known arrangements of mercury electrodes with constant surface area lies in that the temperature of mercury used as an electrode is changing in dependence of environmental effects and simultaneously the magnitude of Faraday-current as a measured signal is also changing, thus the reproducibility of determinations is affected negatively. A further disadvantage of both electrode arrangements lies in that as an electrode material a metal being liquid at room temperature, i.e. mercury, can be applied only.

The object of the present invention is to provide an arrangement for liquid-metal electrode of controllable surface by which said deficiencies of the known electrode arrangements can be eliminated.

The invention is based on the recognition that faults occurring at the electric connection of the liquid-metal electrode can be avoided if at least one section of the capillary is formed within a metal body not reacting chemically with the liquid metal, wherein the metal body serves simultaneously as electric contact means. The metal body contacts the liquid-metal on a large surface, as a consequence electric connection with low resistance and high operative safety can be obtained.

The metal body can advantageously fulfill the task of a valve seat for the valve of the electrode arrangement, in this case an elastic closing element of the valve fits to a surface of the metal body surrounding an opening of the capillary section formed therein. As an elastic closing element preferably silicone rubber is used. The simultaneous application of the properly shaped metal body and the closing element made of silicone rubber results in a long useful life and safe operation of the valve, even in the case of the electrode arrangement is out of operation for a relatively long period, i.e. the valve is kept in closed position and then repeatedly put into operation.

The metal body can be well used for fixing the capillary tube made of an insulating material, e.g. of glass, forming the other section of the capillary, said other capillary section is fixed to the metal body e.g. by gluing so that the two capillary sections are continuations of each other. Inner diameters of the two capillary sections can be equal, however, the capillary section within the metal body may have a larger inner diameter. In such a manner production and assembly can be facilitated and danger of clogging can be reduced, too.

For the electrode arrangement according to the invention capillaries with larger inner diameters can be used in comparison to classical polarographic glass capillaries. The inner diameter of the glass capillary section may amount to 50-300 μm, while the inner diameter of the capillary section within the metal body may equal to 200-600 μm. The advantage of the larger diameter lies in that sensitivity of determinations can be increased, application of liquid-metal of high purity is not required.

The application of the metal body brings the advantage that, when built together with a thermostat, ideal heat transfer can be obtained. In such a manner thermostating of the liquid-metal becomes possible, at the same time errors of the measured signal resulting from changes in temperature can be eliminated. Consequently, surfaces of electrode drops produced one after the other will be approximately equal.

In an especially preferred embodiment the metal body is attached to the liquid-metal reservoir so that a part of the metal body carrying the surface serving as a valve seat extends into the reservoir, and at this part of the metal body a thermostating metal block provided with a heating element and a temperature sensor is arranged, the heating element and the temperature sensor being connected to a regulating unit. With this embodiment both the liquid-metal contained in the reservoir and the liquid-metal filament contained in the capillary are thermostated.

Accuracy of the measurement can be further increased by means of an embodiment having a measuring cell which is also thermostated. For this purpose the measuring cell is surrounded with a further thermostating metal block provided with a further heating element and a further temperature sensor, the further heating element and temperature sensor being also connected to the regulating unit. Temperature of thermostating can be set by using a properly controllable regulating unit. In such a manner by the aid of a control and data processing unit temperature-dependence of the measured signal can be determined by measurements carried out at different temperatures. By increasing thermostating temperature above room temperature, it becomes possible to use instead of mercury a metal, e.g. gallium which is solid at room temperature but has a low melting point.

The metal drop formed at the end of the capillary of the electrode arrangement according to the invention can be removed after having finished measuring by means of a drop dislodging device provided with a hammer impacting on the glass capillary or the metal body, the actuation of which is also controlled by the regulating unit well synchronized with the valve control.

The liquid-metal reservoir of the electrode arrangement according to the invention may communicate with a liquid-metal tank assuring a substantially constant hydrostatic pressure. Optionally the tank can be surrounded with a metal thermostat. Volume of the liquid-metal tank can be varied within wide limits, accordingly, the electrode arrangement can be used for a long time without requiring any preparatory work. The liquid-metal tank, the liquid-metal reservoir and their interconnecting tubing are made of a metal or plastic material not reacting chemically with the liquid-metal, so contamination of the liquid-metal serving as an electrode can be avoided.

By using the electrode arrangement according to the invention polarographic determinations can be realized so that a measuring unit connected to the liquid-metal electrode, an auxiliary electrode and a reference electrode arranged in a sample solution within the measuring cell, as well as the regulating unit controlling the valve, the drop dislodging device and optionally the thermostate are connected to a control and data processing unit. With this arrangement the measuring unit forwards the value of the measured signal to the control and data processing unit, which —after having carried out evaluation —gives the command to the regulating unit for dislodging the drop formed at the end of the capillary and for forming the next drop.

By measurings having been performed with the electrode arrangement according to the invention it could be demonstrated that the surface area of the liquid-metal drop, e.g. mercury drop, can be varied within wide limits /e.g. from 0.5 mm$^2$ to about 10 mm$^2$/, while in the course of the measuring the reproducibility of the constant drop surface is very good. Within one measuring series the relative standard deviation amounted to 0.45 % for 100 drops.

Figure 2:
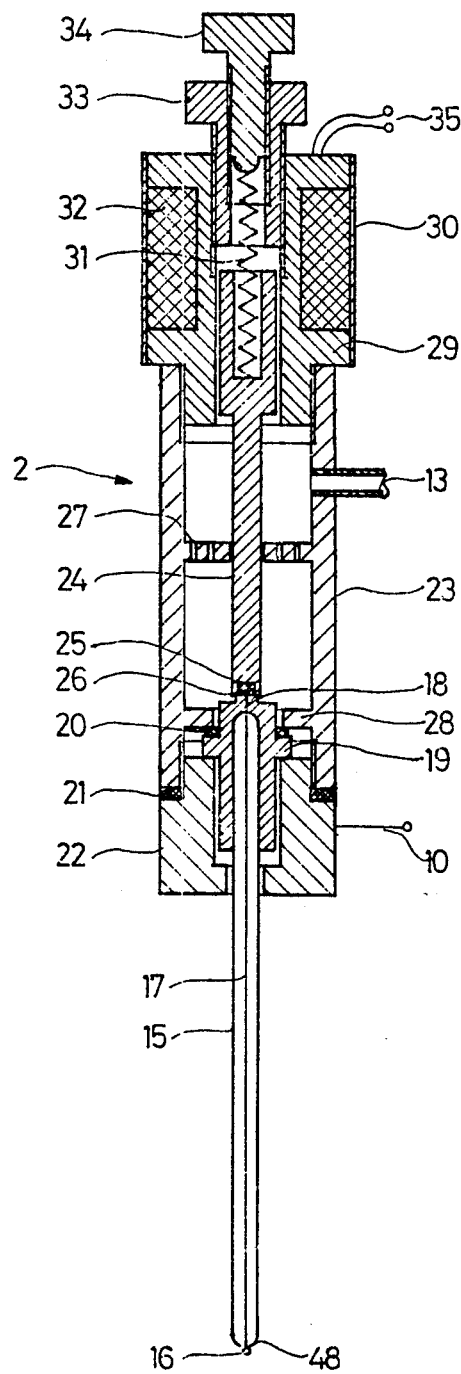
Figure 3:
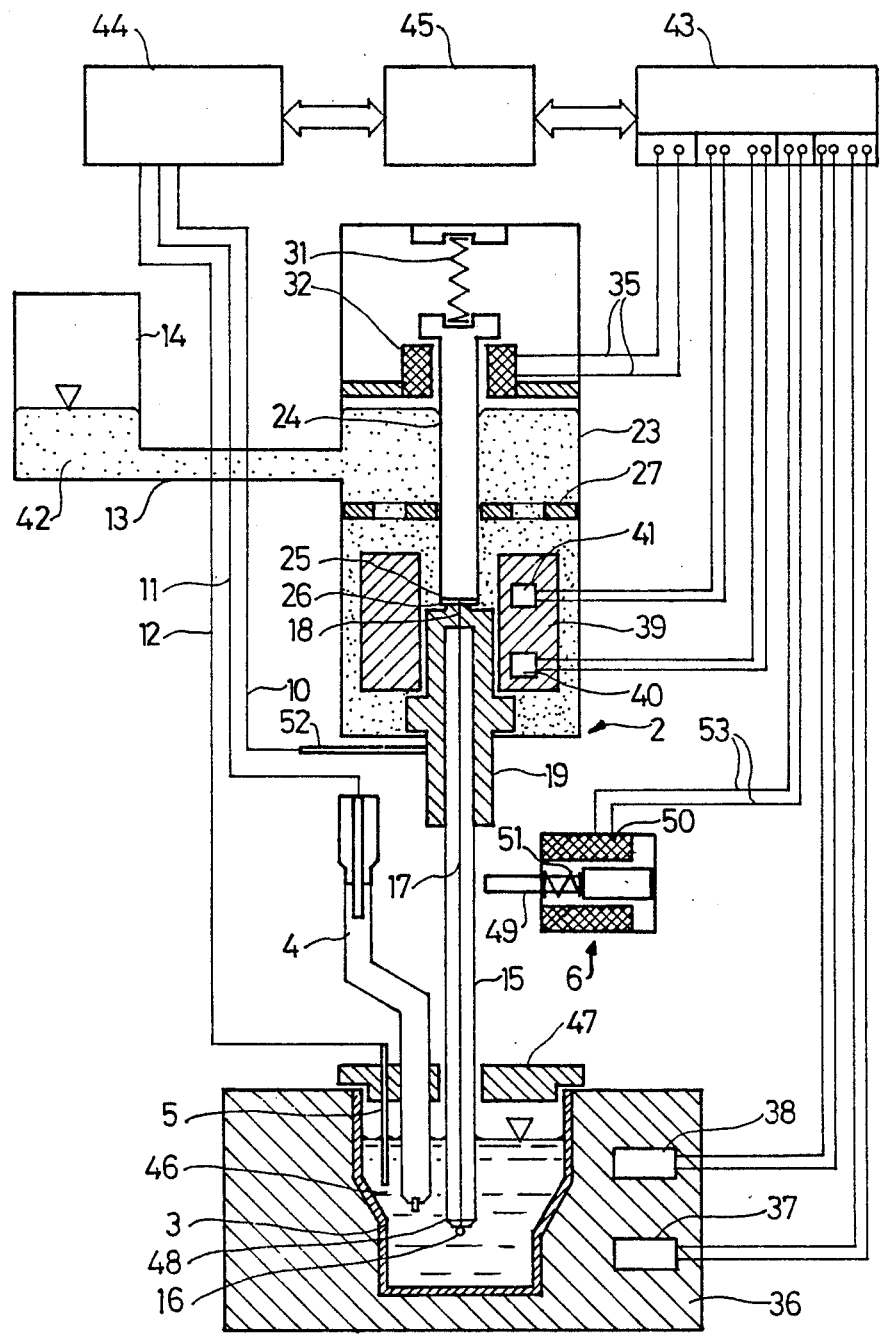

The invention will be described in detail by means of preferred embodiments, with reference to the accompanying drawings, wherein FIG. 1 is a side-view of the embodiment of the electrode arrangement according to the invention, FIG. 2 is a sectional view taken along line A—A of FIG. 1, and FIG. 3 is a schematic view of another embodiment of the electrode arrangement according to the invention.

Identical elements or elements of identical functions are provided with identical reference numbers in the figures.

In FIG. 1 a liquid-metal electrode 2 is carried by a clamping means 7 of a stand 1, wherein a clamping screw 8 clamps the electrode 2. The electrode 2, which is illustrated in detail in FIG. 2, communicates with a liquid-metal tank 14 arranged in the stand 1 via tubing 13. The electrode 2 comprises a glass capillary 15, at one end of which a drop 16 of a liquid-metal, e.g. a mercury drop, is formed. The end extends into a measuring cell 3 which is supported by a holder 9 attached to the stand 1. Furtheron, a reference electrode 4, e.g. a calomel electrode, and an auxiliary electrode 5 extend also into the measuring cell 3. Electric connecting lines 10, 11 and 12 from electrode 2, reference electrode 4 and auxiliary electrode 5, respectively, are led to the stand 1. A measuring unit 44 (see FIG. 3) is connected to the stand 1 by means of an electric connector and cable (not shown).

In the course of measurement the liquid-metal drop 16 formed at the end of the glass capillary 15 is to be torn-off. A drop dislodging device 6 known in itself, attached to the stand 1 and actuated by an electromagnet against a spring, serves for this purpose. When the electromagnet is operated the end of the hammer 49 of the drop dislodging device 6 impacts on the glass capillary 15. Upon the impact the drop 16 falls down.

FIG. 2 illustrates a sectional view of the electrode 2, neither the stand 1 nor the corresponding parts of the measuring cell 3 are shown here. The glass capillary 15 constituting a capillary section 17 is clamped into a metal body 19 and fixed by gluing. Within the metal body 19 a capillary section 18 is formed as a continuation of the capillary section 17. The metal body 19 is fixed to the bottom end of a cylindrical liquid-metal reservoir 23 by means of the flare nut 22. Between an edge 28 of the reservoir 23 extending inwards and a shoulder of the metal body 19 there is a sealing 20, while between the bottom end of the reservoir 23 and the shoulder of the flare nut 22 a further sealing 21 is arranged. Electric connection to the liquid-metal filament in the capillary sections 17 and 18 and thus to the drop 16 is established through the metal body 19, e.g. by means of the line 10 connected to the metal flare nut 22 which again is pressed to the metal body 19.

The surface 26 of the metal body 19 surrounding an opening of the capillary section 18 is formed as a valve seat, the elastic closing element 25 lying on the end of the valve stem 24 is bearing up against said seat. Preferably, the closing element 25 is made of silicone rubber. The upper end of the valve stem 24 comprising a ferromagnetic material is pressed downwards by a spring 31 and upon an electric pulse received through connecting lines 35, the electromagnet formed by coil 32 pulls up said upper end. The coil 32 is arranged on a coil holder 29 made of an insulating material, the latter one is fixed to the upper end of the reservoir 23 with a thread. The coil 32 is covered by a mantle 30 received on the coil holder 29. The length of the upwards travel of the valve stem 24 in the course of opening the valve electromagnetically can be adjusted by means of a screw 33 screwed into the coil holder 29. A further screw 34 is screwed into the screw 33 by the aid of which bias of the spring 31 can be adjusted. Valve stem 24 is guided by a guide disc 27 extending inwards from the wall of the reservoir 23, the disc 27 being provided with openings for the throughflow of the liquid-metal. The liquid-metal reservoir 23 is connected to the liquid-metal tank 14 in the stand 1 via the tubing 13 (FIG. 1).

In the course of measurement the drop 16 formed at the end 48 of the glass capillary 15 forms the liquid-metal electrode. As soon as the drop 16 is consumed, it is torn-off by the drop dislodging device 6 (FIG. 1). Thereafter a pulse of predetermined duration is led to the lines 35, upon which the valve is kept open as long as it is sufficient for the formation of a new drop 16 with the required size and surface area. By changing the duration of the open position of the valve (see FIG. 3, regulating unit 43) any desired area of the surface of the drop 16 can be provided.

The embodiment of FIG. 3 is similar to the embodiment illustrated in FIGS. 1 and 2, however, the stand 1 is not shown here. The reference electrode 4, the auxiliary electrode 5, as well as the end 48 of the glass capillary 15 of the liquid-metal electrode 2 extend into a sample solution 46 contained in the measuring cell 3. The drop 16 of the liquid-metal is formed at the end 48. Measuring cell 3 is covered with a cover 47 and it is surrounded by a thermostating metal block 36, e.g. an aluminum block. For thermostating the metal block 36 is provided with a heating element 37 and a temperature sensory 38 which are connected to a regulating unit 43.

FIG. 3 illustrates the layout of the electrode 2 schematically, only. Connecting means 52 connects the line 10 to the metal body 19. The metal body 19 has a part extending at a certain length into the reservoir 23, which part serves for attching a thermostating metal block 39. The metal block 39 is provided with a heating element 40 and a temperature sensor 41, thermostats partly the liquid-metal contained in the reservoir 23, partly the liquid-metal filament in the capillary sections 17 and 18. Opening of the plate valve constituted by the surface 26 formed as a valve seat and by the closing element 25 made of silicone rubber is carried out by an electric pulse forwarded to the coil 32 by the regulating unit 43 through the lines 35. Subsequent supply of liquid-metal 42 to the reservoir 23 from the tank 14 arrives through the tubing 13. Hammer 49 of the drop dislodging device 6 is actuated against a spring 51 by a coil 50 forming an electromagnet, the control lines 53 of which are also connected to the regulating unit 43.

The electrode 2, the reference electrode 4 and the auxiliary electrode 5 are connected by the lines 10, 11 and 12 to a measuring unit 44. The regulating unit 43 and the measuring unit 44 are connected to a control and data processing unit 45, this latter one may be a computer. The control and data processing unit 45 determines for the regulating unit 43 the temperature of thermostating of the metal blocks 36 and 39, it gives command for actuating the drop dislodging device 6 and for actuating the plate valve in the electrode 2, simultaneously the duration is also determined during which the regulating unit 43 is keeping the plate valve in its open position. Signals measured by the measuring unit 44 are stored, processed and/or displayed by the control and data processing unit 45 according to necessity.

With the solution according to the invention the area of the surface of the electrode drop can be adjusted by selecting the duration of the open position of the plate valve. Accuracy of adjustment of the electrode drop can be further increased if for the duration of the open position the potential of the electrode 2 is always set back to the same valve with respect to the reference electrode 4. The setting back can be carried out by the measuring unit 44 controlled by the control and data processing unit 45. By these measures the surface tension of the boundary layer between the liquid-metal drop and the same solution can be rendered constant and, as a consequence, change in the measuring electrode potential does not influence the size of the drop through surface tension.

It goes without saying that the invention can be realized in many ways being different from the embodiments as shown. So e.g. the metal capillary section can be arranged in a different way, the metal body 19 may have a different shape, mode of fixing can be different, too, tearing-off of the drop can be solved in any other manner known in itself.

I claim:

1. An electrode arrangement with liquid-metal electrode of controllable surface, comprising
    a reservoir for the liquid-metal having a bottom part,
    a capillary having upstream and downstream ends for producing a liquid-metal drop at said downstream end,
    a metal body for holding said capillary at said upstream end and being attached to said bottom part of said reservoir, said metal body comprising a capillary section formed therein as a continuation of said capillary and having a surface surrounding an opening of said capillary section, a controllable valve for passing the liquid-metal selectively from said reservoir to said capillary passage, said valve including an elastic closing element fitting to said surface of said metal body, connecting means for establishing an electric contact to said metal body, thermostating means for controlling the temperature of the liquid-metal, and a drop dislodging device to dislodge the liquid-metal drop produced at said downstream end of said capillary.

2. The electrode arrangement as claimed in claim 1, wherein said elastic closing element is made of silicone rubber.

3. The electrode arrangement as claimed in claim 1, wherein said capillary is formed by a glass capillary which is fixed to said metal body so that said glass capillary and said capillary section are continuations of each other and the inner diameter of said capillary section is at least as large as the inner diameter of said glass capillary.

4. The electrode arrangement as claimed in claim 3, wherein the inner diameter of said glass capillary is 50 to 300 μm and the inner diameter of said capillary section is 200 to 600 μm.

5. The electrode arrangement as claimed in claim 1, wherein said metal body is attached to said bottom part of said reservoir so that a part of said metal body having said surface extends into said reservoir, and a thermostating metal block is arrangement at said part of said metal body, said thermostating metal block being provided with a heating element and a temperature sensor, and the arrangement further comprises a temperature regulating unit to which the heating element and the temperature sensor are connected.

6. The electrode arrangement as claimed in claim 5, further comprising a measuring cell containing a reference electrode and wherein said downstream end of said capillary extends into the measuring cell containing the reference electrode, and a further metal block surrounding the measuring cell and provided with a further heating element and a further temperature sensor, said further heating element and said further temperature sensory being connected to said temperature regulating unit.

7. The electrode arrangement as claimed in claim 3, wherein said drop dislodging device is actuated electromechanically and attached to said metal body or to said glass capillary, said valve is an electromagnetic valve, and said drop dislodging device and said valve have control lines connected to a regulating unit.

8. The electrode arrangement as claimed in claim 1, wherein said reservoir is connected to a liquid-metal tank ensuring a substantially constant liquid pressure.

9. The electrode arrangement as claimed in claim 1, further comprising an electronic unit applying a constant electric potential onto said metal body during open positions of said valve.

* * * * *